US011219522B2

(12) United States Patent
Rengarajan et al.

(10) Patent No.: US 11,219,522 B2
(45) Date of Patent: Jan. 11, 2022

(54) SYSTEMS AND METHODS OF TREATING MALFUNCTIONING CARDIAC VALVES

(71) Applicants: THE JOHNS HOPKINS UNIVERSITY, Baltimore, MD (US); BOSTON SCIENTIFIC SCIMED, INC., Maple Grove, MN (US)

(72) Inventors: Ramji Rengarajan, Santa Rosa, CA (US); Victor San Hou Yu, Guangdong (CN); Kalyna Sconzert, Minneapolis, MN (US); Tom Jancaric, Maple Grove, MN (US); Reggie Roth, Monticello, MN (US); James Cawthra, Ramsey, MN (US); Dennis Werner, Big Lake, MN (US); Jason Kilvington, Shoreview, MN (US); Umang Anand, Plymouth, MN (US); George L. Coles, Baltimore, MD (US); James Duncan Beaty, Sandy Hook, CT (US); Keith Bulkin, New Market, MD (US); Joseph A. Walters, Aberdeen, MD (US); Timothy P. Harrigan, Franklin, MA (US); Kenton J. Zehr, Baltimore, MD (US); Todd Christopher Crawford, Baltimore, MD (US)

(73) Assignees: THE JOHNS HOPKINS UNIVERSITY, Baltimore, MD (US); BOSTON SCIENTIFIC SCIMED, INC., Maple Grove, MN (US)

( * ) Notice: Subject to any disclaimer, the term of this patent is extended or adjusted under 35 U.S.C. 154(b) by 70 days.

(21) Appl. No.: 16/617,044

(22) PCT Filed: May 25, 2018

(86) PCT No.: PCT/US2018/034593
§ 371 (c)(1),
(2) Date: Nov. 26, 2019

(87) PCT Pub. No.: WO2018/218121
PCT Pub. Date: Nov. 29, 2018

(65) Prior Publication Data
US 2021/0128298 A1 May 6, 2021

Related U.S. Application Data

(60) Provisional application No. 62/511,615, filed on May 26, 2017.

(51) Int. Cl.
A61F 2/24 (2006.01)

(52) U.S. Cl.
CPC .... A61F 2/2421 (2013.01); A61F 2220/0016 (2013.01); A61F 2230/0067 (2013.01)

(58) Field of Classification Search
CPC .... A61F 2/2421; A61F 2/2427; A61F 2/2469; A61F 2/2476; A61F 2220/0008;
(Continued)

(56) References Cited

U.S. PATENT DOCUMENTS

| 6,764,510 B2 | 7/2004 | Vidlund et al. |
| 2007/0093890 A1 | 4/2007 | Eliasen et al. |

(Continued)

OTHER PUBLICATIONS

International Search Report and Written Opinion issued in PCT/US18/34593 filed May 25, 2018 (12 pages).

Primary Examiner — Paul B Prebilic
(74) Attorney, Agent, or Firm — BakerHostetler

(57) ABSTRACT

A buoy system for treating cardiac valve regurgitation comprising a movable plug having atrial and ventricular ends, wherein a through-hole passes from the atrial to the ventricular end, wherein during systole, the plug travels toward a cardiac atrium, wherein during diastole, the plug travels into a cardiac ventricle; a tether having atrial and (Continued)

ventricular ends, wherein the tether passes through the through-hole of the moving plug, wherein the atrial end of the tether projects into an atrium, wherein the atrial end of the tether includes a cap to engage a delivery tool; at least one distal anchor located in the ventricle, wherein the distal anchor is coupled to the ventricular end of the tether, and wherein the system is percutaneously delivered and optionally recaptured via catheter and recapture tool at the cap of the tether, respectively.

26 Claims, 10 Drawing Sheets

(58) Field of Classification Search
CPC ...... A61F 2220/0016; A61F 2220/0075; A61F 2230/0067; A61F 2230/0069; A61F 2230/0086; A61F 2230/0091; A61F 2230/0093; A61F 2250/0008; A61F 2250/0039; A61F 2250/0069
See application file for complete search history.

(56) References Cited

U.S. PATENT DOCUMENTS

| | | | |
|---|---|---|---|
| 2011/0077733 A1* | 3/2011 | Solem | A61N 1/056 623/2.12 |
| 2011/0178534 A1 | 7/2011 | Whitman et al. | |
| 2012/0143320 A1 | 6/2012 | Eliasen et al. | |
| 2013/0190798 A1* | 7/2013 | Kapadia | A61F 2/2466 606/195 |
| 2013/0325110 A1 | 12/2013 | Khalil et al. | |
| 2013/0338763 A1* | 12/2013 | Rowe | A61F 2/2427 623/2.11 |
| 2013/0338764 A1 | 12/2013 | Thornton et al. | |
| 2014/0336751 A1 | 11/2014 | Kramer | |

\* cited by examiner

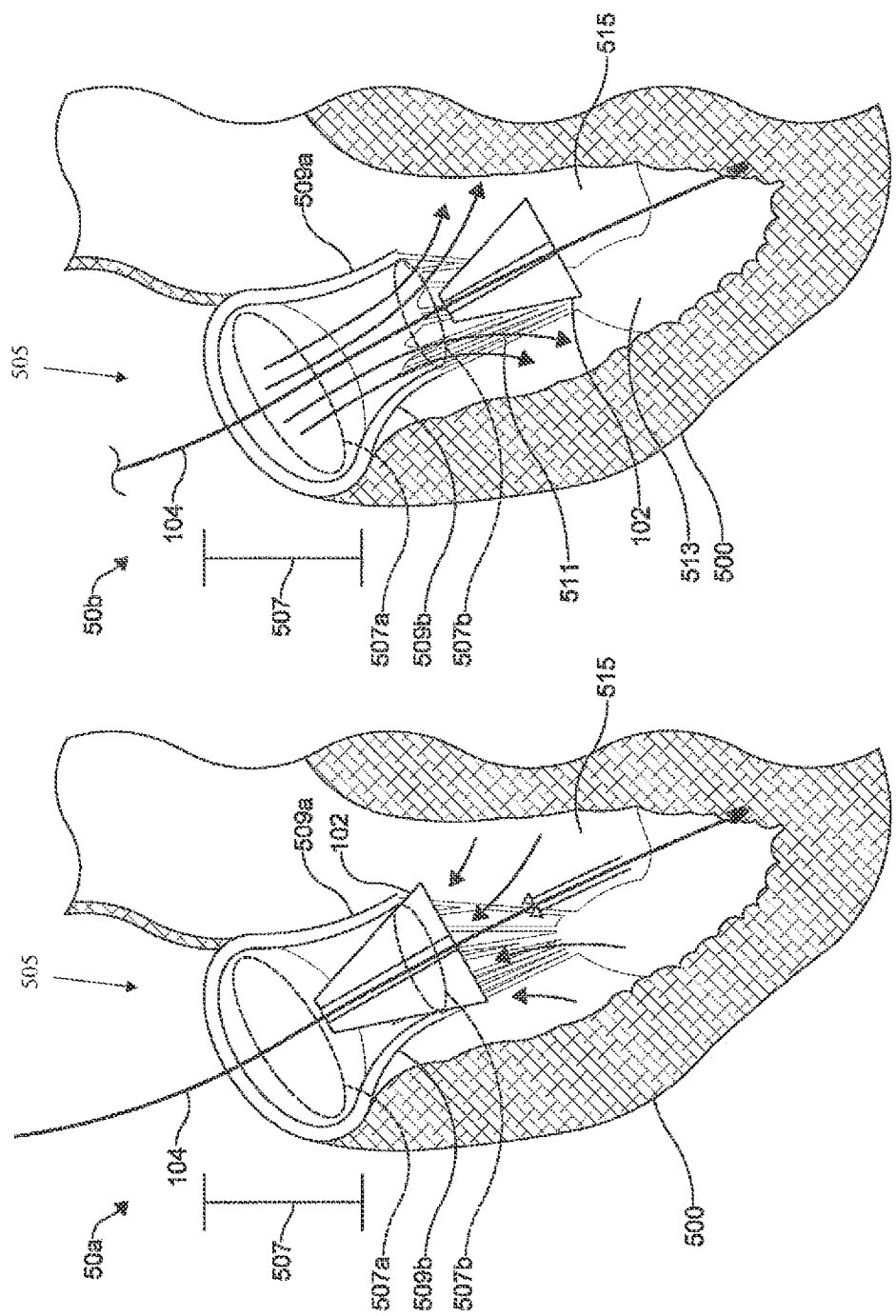

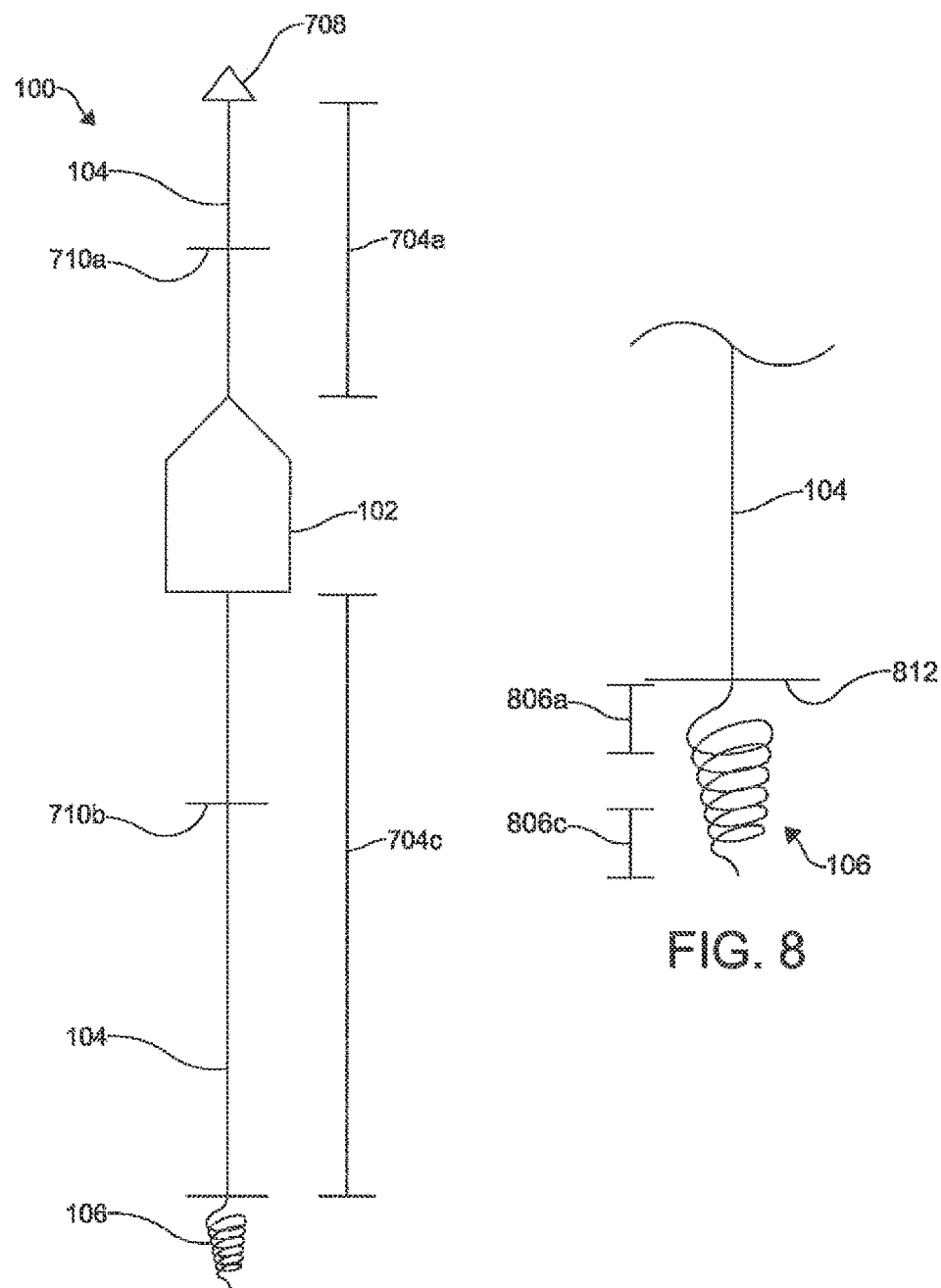

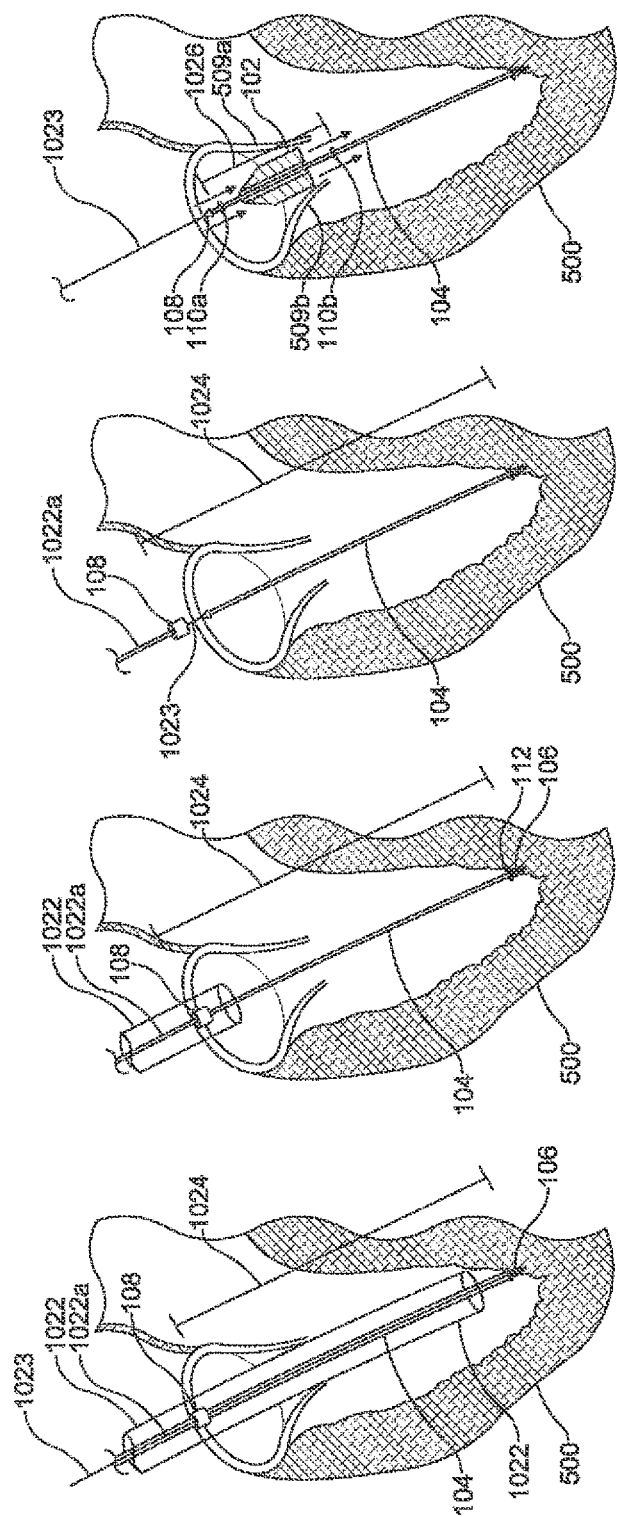

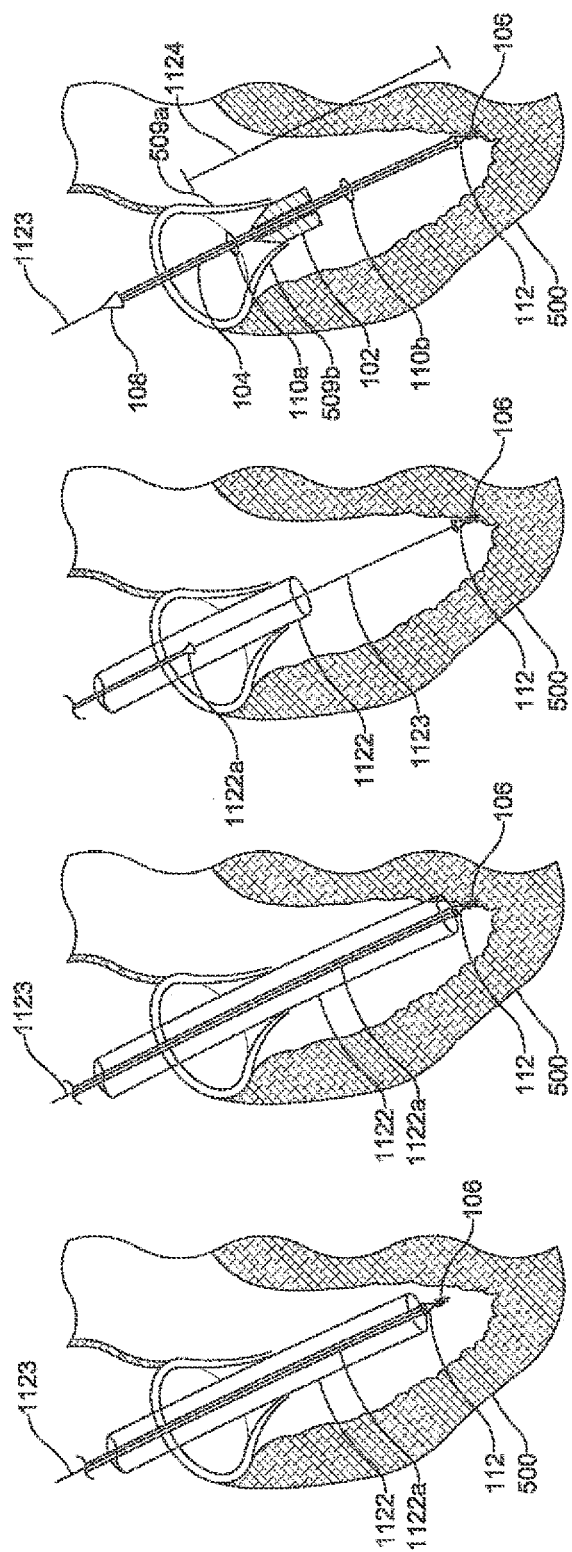

SYSTEMS AND METHODS OF TREATING MALFUNCTIONING CARDIAC VALVES

CROSS-REFERENCE TO RELATED APPLICATIONS

This application is the National Stage of International Patent Application No. PCT/US2018/034593, filed May 25, 2018, which claims the benefit of U.S. Provisional Patent Application No. 62/511,615, filed May 26, 2017, the disclosure of which is incorporated herein by reference in its entirety.

TECHNOLOGICAL FIELD

The present disclosure relates to systems and methods used to treat cardiac valve regurgitation diseases, and more particularly pertains to cardiac valve repair systems used to improve leaflet coaptation and methods for delivery and implementation of the same.

BACKGROUND

A human heart contains four chambers, the left and right atria and left and right ventricles. The atria and ventricles operate through alternate expansion and contraction to pump blood throughout the body. The heart also includes cardiac valves, which function to prevent backflow, or regurgitation of blood from the ventricles into the atria. Improper function of the cardiac valves decreases the efficiency of the heart. That is, a heart with damaged or faulty cardiac valves must perform more work to pump the same amount of blood as a healthy heart with normal cardiac valves, resulting in added stress to the heart. Untreated cardiac valve regurgitation may lead to an increased risk of congestive heart failure, arrhythmia, or death. Treatment of such a condition typically involves open heart surgery and the repair or replacement of the faulty cardiac valve.

SUMMARY

There is a need for a comparatively less invasive treatment of the damaged or improperly functioning cardiac valve. The need further includes a safe device used to treat valve regurgitation. Specifically, such a need includes a percutaneous repair system that avoids replacement of the valve. The present devices and method address these and other shortcomings of the art.

The present disclosure relates to systems and methods for delivery and recapture of cardiac valve devices in the form of a cardiac valve plug. In one aspect, a buoy system for treating cardiac valve regurgitation comprises a tether element having an atrial end and a ventricular end, wherein the atrial end of the tether element projects into an atrium of a heart, wherein the atrial end of the tether element includes a cap; and a plug having an atrial end and a ventricular end. The tether element may pass through a through-hole of a plug. During a systolic phase of a cardiac cycle, the plug travels along the tether toward a cardiac atrium. During a diastolic phase of the cardiac cycle, the plug travels along the tether toward and into a cardiac ventricle.

In another aspect, a buoy system for treating cardiac valve regurgitation is disclosed, whereby a plug is caused to land across the cardiac valve in systole and serves to block backflow into the atrium. The buoy system, according to certain aspect, may comprise a plug having an atrial end and a ventricular end, wherein a through-hole passes from the atrial end to the ventricular end. During a systolic phase of a cardiac cycle, the plug travels toward a cardiac atrium. During a diastolic phase of the cardiac cycle, the plug travels toward and into a cardiac ventricle. As an example, a tether element having an atrial end and a ventricular end passes through the through-hole of the plug in use, the atrial end of the tether element may project into the atrium of the heart. The atrial end of the tether element may include a cap. At least one distal anchor may be located at the cardiac ventricle, wherein the at least one distal anchor is coupled to the ventricular end of the tether element. The at least one distal anchor may be attached at a ventricular location of the heart. The buoy system may be percutaneously delivered via a delivery catheter. Optionally, the buoy system may be percutaneously recaptured via a delivery and recapture tool at the cap of the tether element.

BRIEF DESCRIPTION OF THE FIGURES

The accompanying drawings, which are incorporated in and constitute a part of this specification, illustrate embodiments and together with the description, serve to explain the principles of the methods, devices, and systems.

FIGS. 5A-5B illustrate an example buoy system disposed in a heart.
FIG. 7 illustrates an example buoy system.
FIG. 8 illustrates an enlarged view of an anchor of the buoy system of FIG. 7.
FIGS. 10A-10D illustrate an example buoy system and methods of using the same in a heart.
FIGS. 11A-11D illustrate an example buoy system and methods of using the same in a heart.

DETAILED DESCRIPTION

The present disclosure relates to systems and methods used to treat cardiac valve regurgitation diseases, and more particularly pertains to cardiac valve prostheses in the form of implants that improve leaflet coaptation and methods for delivery and implementation of the same. A buoy system described herein may suitably be used in connection with the treatment and/or the repair of an improperly functioning cardiac valve and corresponding valve regurgitation.

Buoy System

Figure 1:
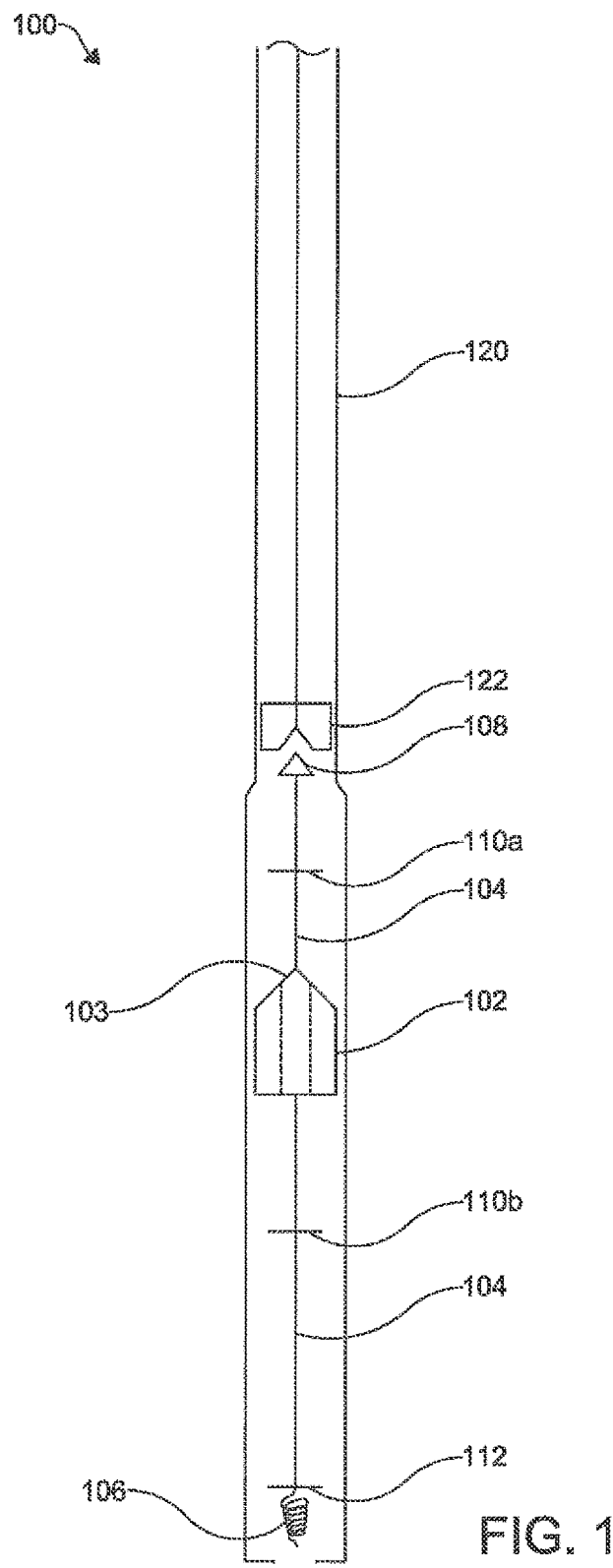
FIG. 1 is a schematic drawing of an example buoy system.

Referring to FIG. 1, a buoy system 100 for treating cardiac valve regurgitation is depicted. As shown, the buoy system 100 may generally include a plug 102 which is coupled to, and travels along a tether element 104, the tether element 104 passing through a through-hole 103 extending within the length of the plug 102, the tether element 104 also being coupled to a fixed anchor 106 at one end. The tether element 104 may include a cap 108 used to interface with the delivery and recapture tool for delivery and recapture of the system. The cap 108 may be disposed at an end opposite the anchor 106. Plug stoppers 110a, 110b may limit travel of the plug 102 along the tether element 104. The plug stoppers 110a, 110b limit the plug 102 to a consistent distance of travel during each cardiac cycle such that the plug 102 concludes movement at a location relatively central to a cardiac valve annulus. Atrial plug stopper 110a may be disposed along the tether element 104 such that during systole, the plug 102 is partially disposed above a valve annulus and partially disposed below the valve annulus. Ventricular plug stopper 110b may be disposed along the tether element 104 within a heart ventricle. During diastole, the plug 102 may completely clear the terminal edges, or ends of the leaflets, and is disposed entirely with a heart ventricle. Due to the placement of the ventricular plug stopper 110b, the plug 102 does not travel further along the tether element to reach the anchor portion of the system. An anchor stopper 112 limits the depth of placement of the anchor 106 in the ventricle and provides tactile feedback to an individual delivering the system. As used throughout, it is understood that the anchor 106 and the anchor stopper 112 may be configured as an anchor assembly. As such, reference to the anchor 106 may include the anchor 106 and the anchor stopper 112 and reference to the anchor stopper 112 may include the anchor 106 and the anchor stopper 112.

As noted above, a delivery system 120 is used to deliver the buoy system 100. Delivery of a delivery and recapture tool 122 and the buoy system 100 may occur percutaneously. In a further aspect, the delivery and recapture tool 122 engages the cap 108 of the tether element 104 to deliver the buoy system 100. In yet another aspect, the delivery and recapture tool 122 engages the cap 108 of the tether element 104 to recapture the self-centering buoy system 100.

Plug

Figure 2:
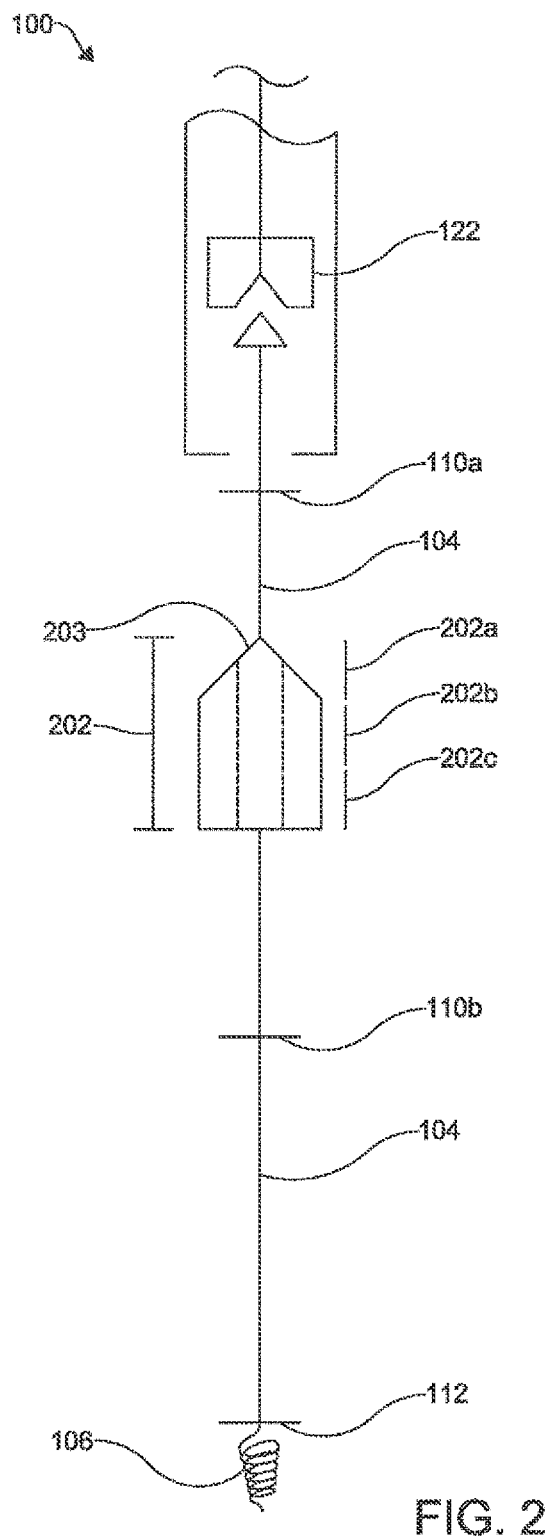
FIG. 2 is a schematic drawing of the system of FIG. 1.

Referring to FIG. 2, a rendering of the structure of a self-centering buoy system 100 is depicted.

As shown, the structure of the plug 202 includes an atrial end 202a, a coaptation zone 202b, a ventricular end 202c, and a through-hole 203. The atrial end of the plug 202a is configured to face a heart atrium, and is further geometrically configured to cross a cardiac valve annulus with ease. The coaptation zone 202b of the plug further includes an atrial end and a ventricular end. The atrial end of the coaptation zone 202b is configured to face a heart atrium and the atrial end of the plug 202a. The ventricular end of the coaptation zone 202b is configured to face a heart ventricle and the ventricular end of the plug 202c. The coaptation zone 202b is further configured to permit coaptation by cardiac valve leaflets, thereby forming a barrier, or seal between a heart atrium and ventricle. The ventricular end of the plug 202c is configured to face the apex of the heart and is positioned perpendicular to the direction of flow of blood, while never leaving the ventricle. Such configuration is necessary to push the plug toward the atrium using the force of blood flow pushing against the plug 202c. In certain aspects, the ventricular end of the plug 202c may be flat. In an aspect, the ventricular end of the plug 202c may be convex. In another aspect, the ventricular end of the plug 202c may be concave. The through-hole of the plug 203 extends from the atrial end of the plug 202a to the ventricular end of the plug 202c, and is configured with low clearance so as to fit with a tether element 104 and limit ingress of blood against the stream of blood flow.

All descriptions of diameter below are presented as relative to other diameters within the same structure. The various shapes described herein are designed with the understanding that shape and dimensions of the plugs may be patient specific. It is understood that various combinations of the configuration described may be used.

Figure 3A:
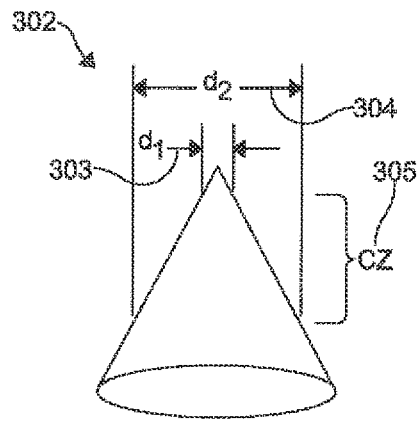
FIGS. 3A-3F illustrate various aspects of a plug.

Referring to FIG. 3A, a rendering of a conical plug 302 is depicted. In an aspect, the atrial end of the plug tapers from a first, relatively narrow diameter 303 to a second, relatively wide diameter 304. The coaptation zone 305 of the conical plug 302 forms a conical shape, with a narrow diameter 303 facing the atrial end and the wider diameter 304 facing the ventricular end. In certain aspects, the ventricular end of the plug 302 is flat.

Figure 3B:
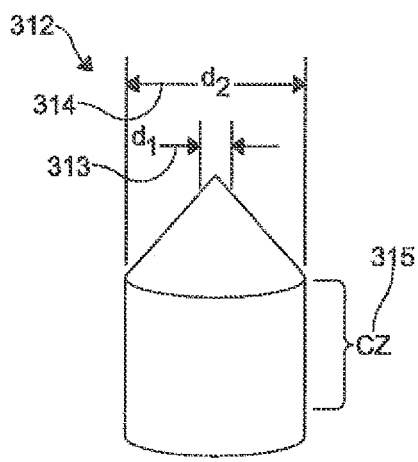

Referring to FIG. 3B, a rendering of a conical-cylindrical plug 312 is depicted. In an aspect, the atrial end of the plug is conical. That is, the atrial end of the plug tapers from a first, relatively narrow diameter 313 at the atrial end to a second, relatively wide diameter 314 toward the coaptation zone 315. In an aspect, the coaptation zone 315 forms a cylinder. Each of the atrial and ventricular ends of the coaptation zone 315 has the same diameter. In an aspect, the coaptation zone diameter is equal to the second, relatively wide diameter 314. In another aspect, the coaptation zone diameter is greater than the second diameter 314. In certain aspects, the ventricular end of the plug 312 is flat.

Figure 3C:
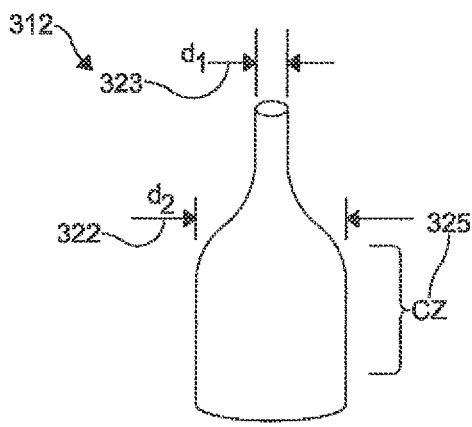

Referring to FIG. 3C, a rendering of a bottleneck plug 322 is depicted. In an aspect, the atrial end of the plug forms a first, relatively narrow diameter 323 and extends lengthwise from the atrial end of the plug toward the ventricular end of the plug. The coaptation zone 325 of the bottleneck plug forms a cylinder shape with a relatively wide second diameter 324. Thus, each of the atrial and ventricular ends of the coaptation zone 325 includes the second diameter 324. In certain aspects, the ventricular end of the plug 322 is flat.

Figure 3D:
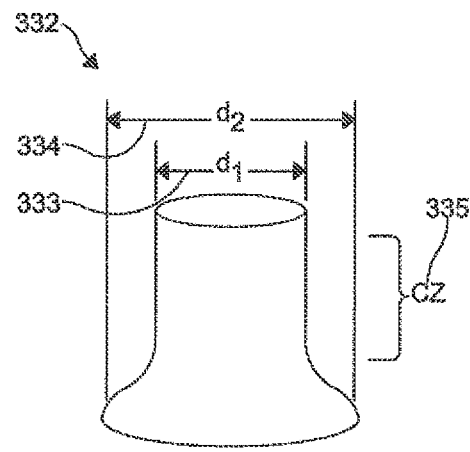

Referring to FIG. 3D, a rendering of a cylindrical-winged plug 332 is depicted. In an aspect, the atrial end of the plug is longitudinally extended toward the ventricular end of the plug. The atrial end of the plug forms a first diameter 333. The coaptation zone 335 of the cylindrical-winged plug forms a cylindrical shape in which each of the atrial and ventricular ends of the coaptation zone 335 includes the first diameter 333. The ventricular end of the cylindrical-winged plug forms a second, relatively wide diameter 334 and may be disposed entirely within the ventricle. In certain aspects, the ventricular end of the plug 332 is flat.

Figure 3E:
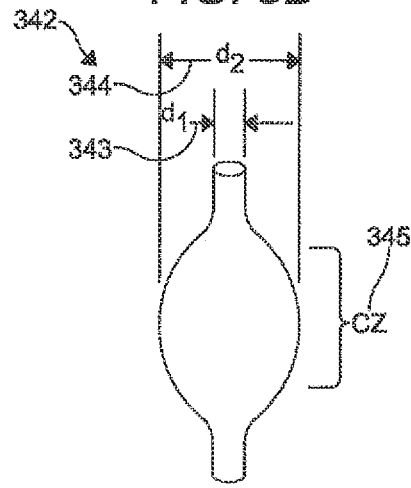

Referring to FIG. 3E, a rendering of a spherical-ovoid plug 342 is depicted. In an aspect, the atrial end of the plug is tapered from a first, relatively narrow diameter 343 to a second, relatively wide diameter 344 at the coaptation zone 345. The coaptation zone 345 forms a spherical-ovoid, or bulbous shape, and may taper to form the first diameter 343 at the ventricular end of the plug 342.

Figure 3F:
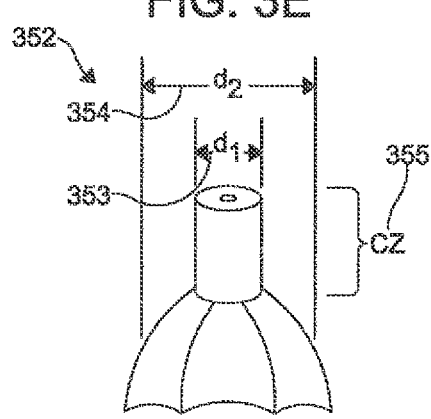

Referring to FIG. 3F, a rendering of a cylindrical-umbrella plug 352 is depicted. In an aspect, the atrial end of the plug is extended longitudinally toward the ventricular end of the plug. The atrial end of the plug includes a first, relatively narrow diameter 353. The coaptation zone 355 of the cylindrical-umbrella plug forms a cylindrical shape such that each of the atrial and ventricular ends includes the first diameter 353. The ventricular end of the plug 352 includes a second, relatively wide diameter 354 and takes the form of an arched, or umbrella shape.

It is understood that the atrial end of the plug illustrated in FIG. 3F may be replaced with any of the configurations illustrated in FIGS. 3A-3E (e.g., so that the ventricular end of any of the configurations of FIGS. 3A-E may have a distal flare). Additionally or alternatively, the atrial end of the plug of FIG. 3B may be combined with any of the configurations of FIGS. 3C-3F.

Figure 4A:
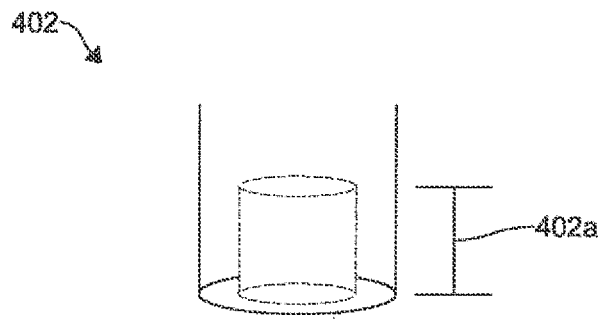
FIGS. 4A-4C illustrate various aspects of a plug with a counter bore.
Figure 4B:
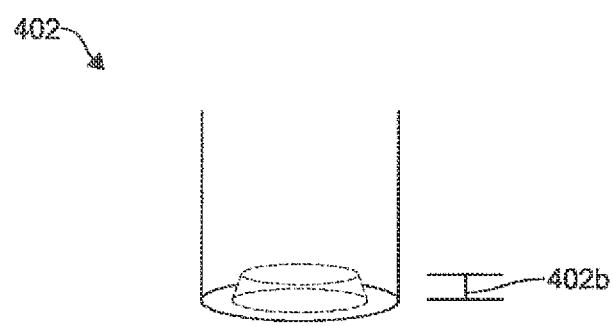
Figure 4C:
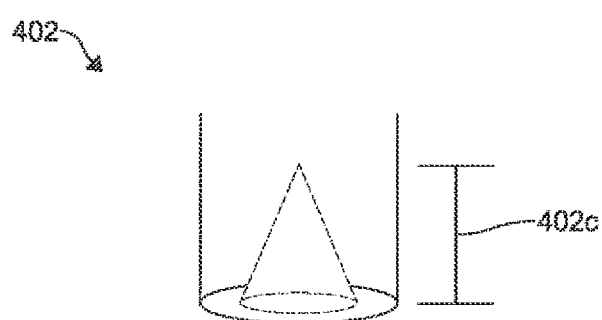

Referring to FIGS. 4A-4C, in certain aspects, the ventricular end of a plug 402 may form a deep-counter bore 402a. A deep counter bore 402a forms a cylindrical recess at the ventricular end of the plug 402. Such a recess is deep relative to a shallow recess 402b at the ventricular end of the plug 402 depicted in FIG. 4B. In an aspect, the shallow recess 402 may taper from a first, relatively, wide diameter at the ventricular end of the plug 402 to a second, relatively narrow diameter at the furthest point of the recess within the plug 402. Referring to FIG. 4C, in an aspect, the ventricular end of a plug 402 may form a conical recess 402c. A conical recess 402c forms a first, relatively wide diameter at the ventricular end of the plug 402 and tapers to a second, relatively narrow diameter, and ultimately tapers to a point at the furthest point within the plug 402.

In certain aspects, the composition of the plug 102 may include various deformable materials so as form a better seal and more readily conform around leaflets of the heart. In an aspect, the surface of the plug 102 is hydrophilic. In an aspect, the plug 102 may comprise a sponge-type foam encased in a flexible membrane, so as to form a malleable, yet impermeable barrier. In another aspect, the plug 102 may comprise a hollow plastic element. In yet another aspect, the plug 102 may be formed of a nitinol frame with a non-porous membrane. In still another aspect, the plug 102 may be formed of a balloon. In an aspect, the plug 102 comprises an activatable, flexible, non-porous membrane. Such a flexible membrane may become inflexible upon activation any one of blood, temperature, or chemical reaction. In yet another aspect, the surface of the plug 102 may be coated with an anti-thrombogenic coating so as to minimize risk of thrombus formation on the plug. In certain aspects, the through-hole 103 of the plug 102 is coated with an anti-thrombogenic material to inhibit thrombus or clot formation in the space formed between the through-hole 103 and the tether element 104. The plug 102 may also be coated with a Teflon™ material so as to reduce drag and friction while moving within the blood field of the heart.

Referring to FIG. 5A, a rendering of the self-centering buoy system 100 functioning within a heart 500 during the systolic phase of the cardiac cycle 50a is depicted. Specifically, in an aspect, the plug 102 is configured to travel along a tether element 104 toward a heart atrium 505 during the systolic phase of the cardiac cycle 50a. In a further aspect, at least a portion of the plug 102 lands relatively centrally aligning with a cardiac valve 507 and corresponding valve annular plane 507a within the heart 500. Such alignment of the plug 102 and the valve annulus 507a results in a barrier created between the cardiac atrium 505 and a cardiac ventricle 515, effectively preventing backflow of blood into the atrium 505. In addition, leaflets 509a, 509b of the cardiac valve 507 coapt onto the plug 102 to form an effective seal against valve regurgitation. Improved coaptation of the leaflets 509a, 509b results from the shared surface of the plug 102 at which the leaflets meet during systole 50a.

Referring to FIG. 5B, a rendering of the self-centering buoy system 100 functioning within a heart 500 during the diastolic phase of the cardiac cycle 50b is depicted. Specifically, in an aspect, the plug 102 travels along a length of the tether element 104 toward the heart ventricle 515 during the diastolic phase of the cardiac cycle 50b. In a further aspect, during diastole 50b, the 102 travels along the tether element 104 into the ventricle 515 of the heart 500. The plug 102 travels a distance such that it clears the annular plane 507a of the cardiac valve 507 within the heart 500. That is, the plug 102 travels within the ventricle 515 at a distance so as to avoid any obstruction across the annular plane of the associated cardiac valve 507a with which the plug 102 aligns during systole 50a. In another aspect, during diastole 50b, the plug 102 travels within the ventricle 515 and is positioned such that the atrial end of the plug 202a is positioned above a plane 507b formed by a set of chordae tendinae 511 and papillary muscles 513 of the heart 500. Thus, during the diastolic phase of the cardiac cycle 50b, the plug 102 does not cause any blockage of blood traveling from the atrium 505 to the ventricle 515 of the heart 500, and full filling of the ventricle 515 is achieved based on the plug retraction.

Figure 6:
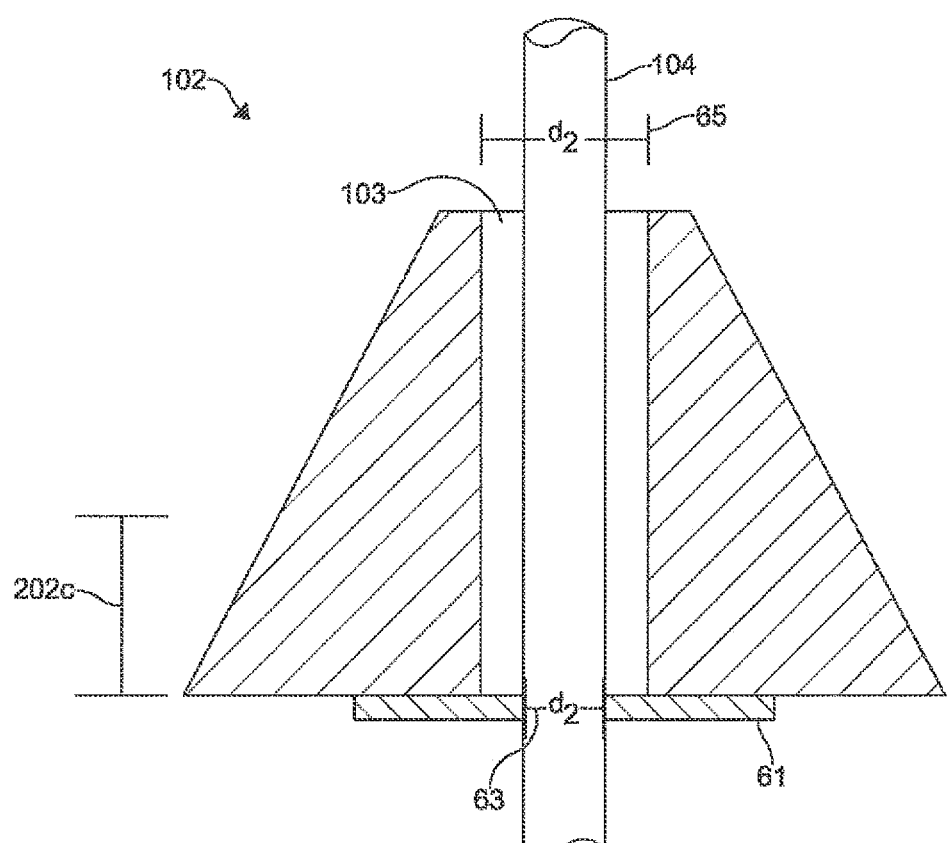
FIG. 6 illustrates an example washer feature.

Referring to FIG. 6, a rendering of a washer feature attachment 61 functioning to clear blood along the tether 104 is depicted. In an aspect, the washer attachment 61 is coupled to the ventricular end 202c of the plug 102 and is configured with a first, relatively narrow diameter 63 in relation to the second, relatively wide diameter 65 of the through-hole 103. The washer attachment 61 facilitates screening and shunting of blood from the junction of the tether element 104 and plug 102 at the through-hole 103. In various aspects, the washer attachment 61 may also be disposed on the plug at the atrial end 202a or built into the plug along the length of the coaptation zone 202b. The washer attachment 61 functions to screen the blood from the through-hole 103 as it moves away from the anchor 106 during systole and as it moves toward the anchor 106 during diastole.

In another aspect, an attachment may be used to clear blood from the through-hole 103 of the traveling plug 102, and thus, prevent thrombus or clot formation at the through-hole 103.

In certain aspects, the plug 102 contains material that renders it visible under various imaging systems. In an aspect, a radiopaque marker may be placed on one or both of a biocompatible plug's atrial 202a and ventricular end 202b. In other various aspects, radiopaque coating of the plug's 102 exterior surface renders the plug visible under C-Arm and x-ray imaging. In yet another aspect, echogenic coating of the plug's 102 exterior surface provides enhanced visibility under echocardiography during delivery, deployment and confirmation of the system. In still a further aspect, a plug 102 comprised of a radiopaque-doped material such as titanium, tungsten, platinum, and Pt-Iridium facilitates visibility under certain imaging systems.

Tether Element

Referring to FIG. 7, a rendering of the structure of a self-centering buoy system 100 with emphasis on a tether element 104 is depicted. As shown, a tether element includes an atrial end 704a and a ventricular end 704c, and is the axis along which the plug 102 rides. In certain aspects, the atrial end 704a of the tether element 104 includes a feature configured to align and self-center the tether 104 with blood flow. In an alternative aspect, a cone at the atrial end 704a of the tether element 104 facilitates alignment with blood flow. Such alignment of the tether element 104 with the flow of blood functions to center the buoy system 100 within the cardiac valve 507 and facilitates optimal leaflet coaptation. In an aspect, the tether element 104 controls direction of the plug 102 based on its pass through the through-hole 103 of the plug. In an aspect, the atrial end 704a of the tether element 104 projects into the atrium 505 of the heart 500. In certain aspects, the atrial end 704a of the tether element 104 includes a cap 708 configured to interface with a delivery and recapture tool 122.

In various further aspects, various forms of capture mechanisms utilized by the cap 108 may include, but are not limited to, a hook and eyelet configuration, a ball catch mechanism, an interlocking pin mechanism, and a screw mechanism.

In certain aspects, the atrial end 704a of the tether element 104 includes an atrial anchor. In a further aspect, the atrial anchor is attached at a cardiac atrial wall. In various alternative aspects, the atrial anchor is attached at one of an inferior vena cava, a superior vena cava, or with a surgically placed stent.

In various aspects, the tether element 104 includes an atrial stopper 710a and a ventricular stopper 710b. The atrial stopper 710a is located at a desired distance proximal to the plug 102, in a direction away from the anchor 106. Similarly, the ventricular stopper 710b is located at a desired distance distal to the plug 102, in a direction toward the anchor 106. Such placement of stoppers 710a, 710b functions to limit the travel distance of the plug 102 to that which is appropriate for the anatomy of the particular heart 500 in question, and are positioned so as to maintain a consistent distance of travel of the plug 102. In an aspect, at least one stopper 710a, 710b is adjustable in at least one of a proximal direction away from the anchor 106 or a distal direction toward the anchor. As shown in FIG. 7, the ventricular end 704c of the tether element 104 is fixed to an anchor 106 at a distal end of the buoy system 100.

In certain aspects, the tether element 104 may be entirely composed of a solid material, or it may have a flexible portion of variable length.

In alternative aspects, the tether element 104 may comprise an inflexible rod portion upon which the plug 102 may travel. In an aspect, the ventricular end of the tether element 704c may comprise a flexible material coupled to the inflexible, atrial rod portion of the tether 104. Thus, in certain aspects, the flexible portion of the tether element 104 facilitates the reduction of force exerted on the distal end of the system 100. In an aspect, the ventricular, flexible portion of the tether element 104 facilitates the self-centering capability of the system 100 by providing a point around which the tether element 104 may pivot in order to land in the regurgitant flow. In an aspect, the ventricular, flexible portion of the tether element 104 may act as a dampener so as not to perforate the anchor into the pericardial space.

In an alternative aspect, the tether element 104 includes a threaded portion. The plug 102 of the system 100 may be configured to travel along the threaded portion, and the distance of travel of the plug 102 may be limited by the length of the threaded portion of the tether element 104.

In still a further aspect, the tether element 104 includes a rifling pattern. The plug 102 of the system 100 may be configured to travel along the rifled portion, and the distance of travel of the plug 102 may be limited by the length of the rifled portion of the tether element 104.

In certain aspects, the tether element 104 comprises material and markers that render it visible under x-ray or echocardiography imaging of system. In a further aspect, at least one stopper 710a, 710b is comprised of a material visible to C-arm imaging, x-ray imaging, and echocardiography imaging.

Ventricular Anchor

Referring to FIG. 8, a rendering of the structure of a buoy system 100 with emphasis on a ventricular anchor 106 is depicted. As shown, a distal anchor 106 includes an atrial end 806a facing the plug 102 of the system 100, and a ventricular end 806c from which the anchor 106 is attached to the heart 500. In an aspect, the distal anchor 106 is located at the cardiac ventricle 515, and functions to couple the tether element 104 to the heart 500. In an aspect, an anchor stopper 812 is positioned proximal to the distal anchor 106. In an aspect, the anchor stopper 805 is shaped like a washer.

In various aspects, the anchor stopper 812 also functions to provide tactile and visual feedback to prevent excessive penetration of the anchor into and through the ventricular wall during delivery and recapture of the system. In certain aspects, the surface of the anchor stopper 812 is coated or formed with radiopaque and/or echogenic materials. Such properties facilitate visual imaging and ultimately, facilitate correct placement and correct analysis of performance of the system 100. In various aspects, distal anchors 106 are attached at various ventricular locations of the heart 500. In an aspect, the distal anchor 106 is attached at a ventricle 515 of the heart 500. In still a further aspect, the distal anchor 106 is attached at the ventricular apex of the heart. In yet a further aspect, the distal anchor 106 is attached at the septal wall of the heart. In certain aspects, multiple distal anchors 106 are located at the ventricular end 704c of the tether element 704. In an aspect, the distal anchors 86 appear as a tripod, and function to distribute the force exerted by the system 100 on the heart 500.

In certain aspects, the distal anchor 106 may comprise a shock absorbing attachment located at the ventricular end of the tether, proximal to the anchor. The shock-absorbing attachment of the anchor 106 is another method of reducing risk of ventricular perforation based on excessive force exerted upon the anchor, and ultimately, the ventricular cardiac tissue. In a further aspect, the shock-absorbing attachment facilitates the pivoting of the tether element 104 so as to optimize the self-centering property of the system 100.

In various aspects, distal anchors 106 in the present system are capable of unanchoring from an attached location of the heart 500, and are capable of recapture, relocation, or replacement by an alternative system, if necessary.

Distal anchors 106 may be formed in various shapes including one or more of a spring shape, an auger shape, a talon shape, or a fishing hook shape. In an aspect, the structure of the distal anchor 106 includes a plurality of perforations. Perforated anchors permit tissue in-growth and facilitate permanent incorporation into the cardiac tissue. In certain aspects, distal anchors 106 may include at least one barbed end to enhance grip of the system 100 on the cardiac tissue. The surface of the distal anchor 106 may be coated using various techniques to reduce scarring of the endocardial tissue.

Delivery, Deployment, and Recapture System

The delivery system of the present disclosure includes a delivery catheter and a delivery sheath. The delivery catheter forms a relatively narrow diameter and tapers to a larger diameter forming the delivery sheath. The delivery system may be used to house each of a delivery and recapture tool and a buoy system during the implant procedure. The delivery and recapture tool is an elongated body used to engage with a feature on one end of the buoy system. The delivery system is configured so as to allow each of the delivery and recapture tool and the buoy system to pass through each of the relatively narrow diameter and the relatively wide diameter.

Figure 9A:
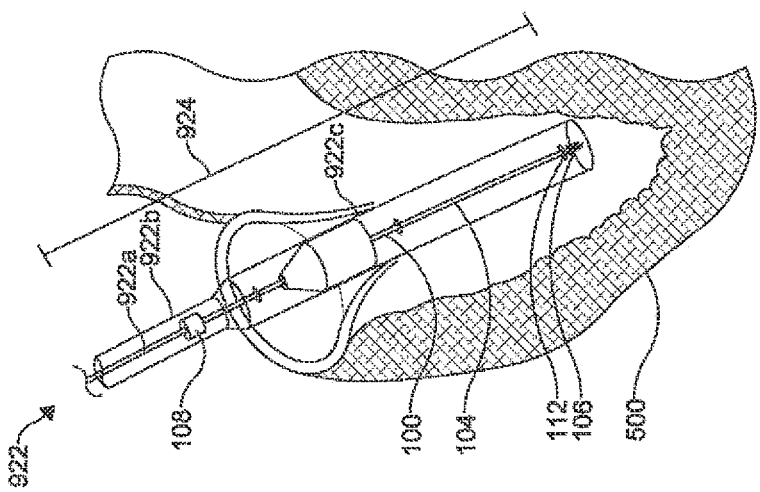
FIGS. 9A-9C illustrate an example buoy system and methods of using the same in a heart.
Figure 9B:
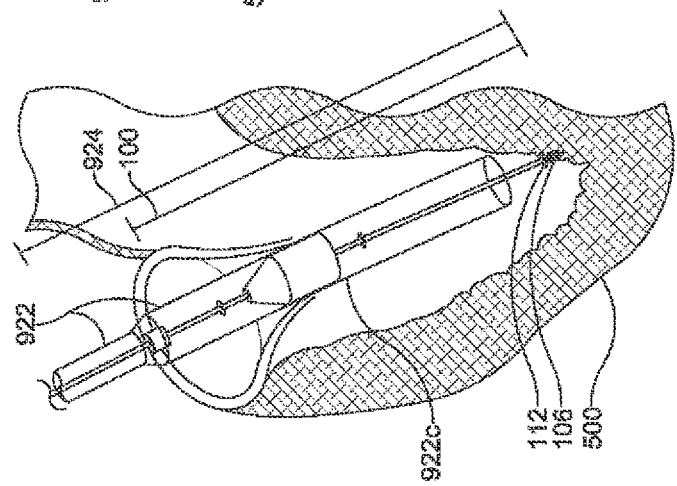
Figure 9C:
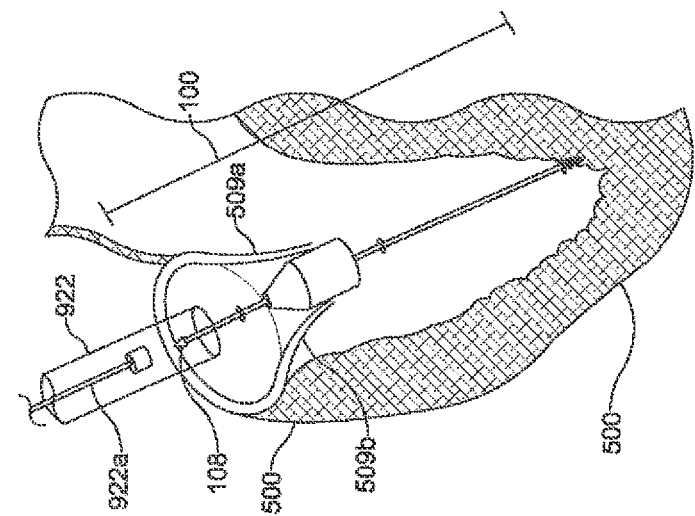

Referring to FIGS. 9A-C, a delivery system 922 of the present disclosure includes a delivery catheter 922b and a delivery sheath 922c. The delivery catheter 922b forms a relatively narrow diameter and tapers to a larger diameter forming the delivery sheath 922c. The delivery system 922 may be used to house each of a delivery and recapture tool 922a and a buoy system 100 during implantation. The delivery and recapture tool 922a is an elongated body with a feature used to engage with a corresponding feature on a tether element 104 at one end of the buoy system 100. The delivery system 922 is configured so as to allow each of the delivery and recapture tool 922a and the buoy system 100 to pass through each of the relatively narrow diameter and the relatively wide diameter.

Referring to FIGS. 9A-C, a rendering of the method of delivery of a buoy system 100 utilizing a delivery system 922 based on relative movement between each system is depicted. The delivery system comprises a delivery catheter 922b and a delivery sheath 922c. The delivery sheath 922c is used as a vessel through which to pass the buoy system 100 for delivery and recapture without damaging itself or other structures in the heart 500. As noted above, the buoy system 100 may move independently of and relative to the delivery system 922. In certain aspects, the delivery system 922 may be used to deliver each of a delivery and recapture tool 922a and the buoy system 100.

Referring to FIG. 9A, the method includes utilizing a delivery system 922 to introduce a delivery and recapture tool 922a and a buoy system 100 into a heart 500 of a patient. In this step, the delivery system 922 may be introduced to a desired location within the heart. Specifically, in an aspect, the delivery and recapture tool 922a and the buoy system 100 may be packaged within the delivery system 922. More specifically, the delivery and recapture tool 922a and the buoy system 100 may be packaged within the delivery catheter 922b and the delivery sheath 922c, respectively. In an aspect, the delivery and recapture tool 922a is connected to the buoy system 100 via a cap 108, or other form of interlocking mechanism at the atrial end of the tether element 104. In still a further aspect, the packaged buoy system 100 and delivery and recapture tool 922a within the delivery system 922 are delivered as an assembly 924.

As noted above, this method may include attaching at least one distal anchor 106 to various ventricular locations within the heart 500. Multiple anchor locations function to distribute force exerted upon the heart and more specifically, the cardiac tissue itself. Such distribution of force reduces the risk of perforation of the cardiac tissue.

Referring to FIG. 9B, after delivery to a desired location within the heart 500, the method further includes anchoring the assembly 924 including the buoy system 100 to a desired location in the ventricular portion of the heart 500. As described above, the buoy system 100 may be anchored at various ventricular locations within the heart 500 of a patient. In an aspect, the assembly 924 may be passed through the delivery sheath 922c and out of the delivery system 922 at the selected location in the heart 500, and at least one distal anchor 106 of the buoy system 100 may be engaged with the cardiac tissue until the user receives tactile feedback from via at least one anchor stopper 112. That is, in an aspect, complete engagement of the buoy system 100 with the cardiac tissue is confirmed by an inability of the user to further advance and engage the distal anchor 106.

Referring to FIG. 9C, after anchoring of the assembly 924 at the selected location within the heart 500, the method further includes the separation of assembly 924 into the original parts, the delivery and recapture tool 922a and the buoy system 100. Upon detachment of the delivery and recapture tool 922a from the buoy system 100, the delivery system 922, including the delivery and recapture tool within, may be withdrawn from the heart 500, and ultimately, from the patient. In an aspect, upon removal of the delivery system 922, the plug 102 of the buoy system 100 is disposed across cardiac valve leaflets 509a, 509b, forming a barrier during systole to improve cardiac valve regurgitation.

In various alternative aspects, the buoy system 100 may be recaptured by introducing the delivery and recapture tool 922a into the heart 500 and engaging the system via a cap 108, or other form of interlocking mechanism.

Referring to FIGS. 10A-D, a rendering of an alternate method of delivery of a buoy system 100 utilizing a delivery catheter 1022 is depicted. The delivery catheter 1022 is used as a vessel through which to pass several components for delivery and recapture without damaging itself or other structures in the heart 500. Notably, the components within the delivery catheter 1022 may move independently of and relative to the catheter itself. In certain aspects, the delivery catheter 1022 may be used to deliver each of a delivery and recapture tool 1022a, guidewire 1023, an anchor-tether assembly 1024, and a stopper-plug-stopper assembly 1026. In an aspect, the delivery and recapture tool 1022a is an elongated body used to engage the cap 108 at an end of a tether element 104 as a portion of a buoy system 100 In an aspect, the guidewire 1023 extends through each of the delivery and recapture tool 1022a and the anchor-tether assembly 1024. In certain aspects, the guidewire 1023 may extend through the tether element 104 of the anchor-tether assembly. In an aspect, the guidewire 1023 may extend through the distal anchor 106 of the anchor-tether assembly. In yet another aspect, the anchor-tether assembly may include at least one anchor stopper 112, at least one distal anchor 106, a tether element 104, and a cap 108, or other form of interlocking mechanism. In certain aspects, the anchor-tether assembly may include an anchor stopper 112. In an aspect, the stopper-plug-stopper assembly 1026 may include a ventricular stopper 110b, a plug 102, and an atrial stopper 110a. The sum of each of the anchor-tether assembly 1024 and the stopper-plug-stopper assembly 1026 form a complete buoy system 100.

Referring to FIG. 10A, the method includes utilizing a delivery catheter 1022 to introduce and deliver a delivery and recapture tool 1022a, a guidewire 1023, an anchor-tether assembly 1024, and a stopper-plug-stopper assembly 1026 at a desired location within the heart 500 of a patient. In this step, the delivery catheter 1022 may be introduced to a desired location within the heart 500. Specifically, in an aspect, the delivery and recapture tool 1022a and the anchor-tether assembly 1024 may be packaged within the delivery catheter 1022. In an aspect, the delivery and recapture tool 1022a is connected to the anchor-tether assembly 1024 via a cap 108 at an end of the assembly opposite the distal anchor 106.

As noted above, this method may include attaching at least one distal anchor 106 with an anchor stopper 112 to various ventricular locations within the heart 500. Multiple anchor locations function to distribute force exerted upon the heart and more specifically, the cardiac tissue itself. Such distribution of force reduces the risk of perforation of the cardiac tissue.

Referring to FIG. 10B, after delivery to a desired location within the heart 500, the method further includes anchoring the anchor-tether assembly 1024 to a desired location in the ventricular portion of the heart 500. In certain aspects, the anchor-tether assembly 1024 may be anchored at various ventricular locations within the heart 500 of a patient. In an aspect, the anchor-tether assembly 1024 may be passed through and out of the delivery catheter 1022 at the selected location in the heart 500, and the distal anchor 106 of the anchor-tether assembly 1024 may be engaged with the cardiac tissue until the user receives tactile feedback from via the anchor stopper 112. That is, in an aspect, complete engagement of the tether-anchor assembly 1024 with the cardiac tissue is confirmed by an inability of the user to further advance and engage the distal anchor 106.

Referring to FIG. 10C, after anchoring of the anchor-tether assembly 1024 at the selected location within the heart 500, the method further includes the detachment of the delivery and recapture tool 1022a from the anchor-tether assembly 1024. Upon detachment of the delivery and recapture tool 1022a from the anchor-tether assembly 1024, the delivery catheter 1022, including the delivery and recapture tool 1022a within, may be withdrawn from the heart 500, and ultimately, from the patient. In an aspect, upon removal of the delivery catheter 1022 and the delivery and recapture tool 1022a, the guidewire 1023 and the anchor-tether assembly remain at the selected location within the heart 500.

Referring to FIG. 10D, after removal of the delivery catheter 1022 and the delivery and recapture tool 1022a, the method further includes introducing the stopper-plug-stopper assembly 1026 into the heart at the location defined by the secured anchor-tether assembly 1024. In an aspect, the ventricular stopper 110b, the plug 102, and the atrial stopper 110a are delivered as the stopper-plug-stopper assembly 1026 over the guidewire 1023. In another aspect, the ventricular stopper 110b, the plug 102, and the atrial stopper 110a are delivered consecutively over the guidewire 1023. Delivery of the full stopper-plug-stopper assembly 1026 over the guidewire and engaging the anchor-tether assembly 1024, form a complete buoy system 100 disposed across cardiac valve leaflets 509a, 509b, forming a barrier during systole to improve cardiac valve regurgitation. In an aspect, following delivery of the full stopper-plug-stopper assembly 1026 and engaging the anchor-tether assembly 1024, the method further includes withdrawing the guidewire 1023 from the heart 500, and from the patient.

In various alternative aspects, the buoy system 100 may be recaptured by introducing the delivery and recapture tool 1022a into the heart 500 and engaging the system via a cap 108, or other form of interlocking mechanism.

Referring to FIGS. 11A-D, a rendering of an alternate method of delivery of a buoy system 100 utilizing a delivery catheter 1122 is depicted. The delivery catheter 1122 is used as a vessel through which to pass several components for delivery and recapture without damaging itself or other structures in the heart 500. Notably, the components within the delivery catheter 1122 may move independently of and relative to the catheter itself. In certain aspects, the delivery catheter 1122 may be used to deliver each of a delivery and recapture tool 1122a, a guidewire 1123, at least one anchor stopper 112, and at least one distal anchor 106 (e.g., an anchor assembly comprising the stopper 112 and the anchor 106, as described herein.) In an aspect, the delivery and recapture tool 1122a is an elongated body used to engage and place the distal anchor 106 at a desired location within the heart 500. In an alternative aspect, the delivery and recapture tool 1122a engages with a feature on the proximal end of an anchor stopper 112 to aid in manipulation and placement of the distal anchor 106 at a desired location within the heart 500. In an aspect, the guidewire 1123 extends through each of the delivery and recapture tool 1122a, the anchor stopper 112, and the distal anchor 106. In certain aspects, the guidewire 1123 may extend through each of the delivery and recapture tool 1122a and the anchor stopper 112. In yet another aspect, the guidewire 1123 may be used to pass along a tether-plug-stopper assembly 1124.

The tether-plug-stopper assembly 1124 may include a tether element 104, a ventricular stopper 110b, a plug 102, and an atrial stopper 110a, and a cap 108, or other form of interlocking mechanism. As an example, the assembly 1124 may lock in with the previously placed anchor assembly. The sum of each of the distal anchor 106, the anchor stopper 112, and the tether-plug-stopper assembly 1124 form a complete buoy system 100.

Referring to FIG. 11A, the method includes utilizing a delivery catheter 1122 to introduce and deliver as a singular structure, a delivery and recapture tool 1122a, a guidewire 1123, an anchor stopper, 112, and a distal anchor 106 at a desired location within the heart 500 of a patient. In this step, the delivery catheter 1122 may be introduced to a desired location within the heart 500. Specifically, in an aspect, the delivery and recapture tool 1122a, the anchor stopper 112, and the distal anchor 106, may be packaged within the delivery catheter 1122. In an aspect, the delivery and recapture tool 1122a is connected to a feature on the anchor stopper 112 (which may be coupled to the anchor, forming an anchor assembly). In an alternative aspect, the delivery and recapture tool 1122a is connected to the distal anchor 106.

As noted above, this method may include attaching at least one distal anchor 106 and at least one anchor stopper 112 to various ventricular locations within the heart 500. Multiple anchor locations function to distribute force exerted upon the heart and more specifically, the cardiac tissue itself. Such distribution of force reduces the risk of perforation of the cardiac tissue.

Referring to FIG. 11B, after delivery to a desired location within the heart 500, the method further includes anchoring the distal anchor 106 and the anchor stopper 112 to a desired location in the ventricular portion of the heart 500. As described above, in an aspect, a guidewire 1123 may pass through one or both of the distal anchor 106 and anchor stopper 112. The guidewire does not anchor to selected portion of the heart 500. In certain aspects, the distal anchor 106 and anchor stopper 112 may be anchored at various ventricular locations within the heart 500 of a patient. In an aspect, the distal anchor 106 and anchor stopper 112 may be passed through and out of the delivery catheter 1122 at the selected location in the heart 500, and the distal anchor 106 may be engaged with the cardiac tissue until the user receives tactile feedback from via the anchor stopper 112. That is, in an aspect, complete engagement of the distal anchor 106 with the cardiac tissue is confirmed by an inability of the user to further advance and engage the anchor.

Referring to FIG. 11C, after anchoring of the distal anchor 106 and anchor stopper 112 at the selected location within the heart 500, the method further includes the detachment of the delivery and recapture tool 1122a from the distal anchor 106. In an aspect, the delivery and recapture tool 1122a may detach from the anchor stopper 112. Upon detachment of the delivery and recapture tool 1122a from the distal anchor 106 or anchor stopper 112, the delivery catheter 1122, including the delivery and recapture tool 1122a within, may be withdrawn from the heart 500, and ultimately, from the patient. In an aspect, upon removal of the delivery catheter 1122 and the delivery and recapture tool 122a, the guidewire 1123, the distal anchor 106, and the anchor stopper 112 remain at the selected location within the heart 500.

Referring to FIG. 11D, after removal of the delivery catheter 1122 and the delivery and recapture tool 1122a, the method further includes introducing the tether-plug-stopper assembly 1124 into the heart at the location defined by the secured distal anchor 106 and anchor stopper 112. In an aspect, the tether element 104, the ventricular stopper 110b, the plug 102, and the atrial stopper 110a, and the cap 108 are delivered as the tether-plug-stopper assembly 1124 over the guidewire 1123. Delivery of the full tether-plug-stopper assembly 1124 over the guidewire 1123 and engaging the distal anchor 106 and anchor stopper 112 form a complete buoy system 100 disposed across cardiac valve leaflets 509a, 509b, forming a barrier during systole to improve cardiac valve regurgitation. In an aspect, following delivery of the full tether-plug-stopper assembly 1124, the method further includes withdrawing the guidewire 1123 from the heart 500, and from the patient.

In various alternative aspects, the buoy system 100 may be recaptured by introducing the delivery and recapture tool 1122a into the heart 500 and engaging the system via a cap 108, or other form of interlocking mechanism.

In certain aspects, the delivery tool 922a, 1022a, and 1122a used in the methods described above modifies either or both of the shape of the plug 102 or the position of the plug 102. In a further aspect, the delivery tool 922a, 1022a, and 1122a may expand or inflate the plug 102. In one aspect, the delivery tool 922a, 1022a, and 1122a may unsheathe a nitinol mesh frame, which may expand to form the predetermined and desired shape.

In various aspects, the self-centering buoy system 100 may be evaluated and analyzed for proper placement as well as for efficient and proper function. To confirm proper placement and function of the system, various imaging techniques may be used. In an aspect, ultrasound imaging may be used. In a further aspect, fluoroscopy imaging is preferred whereby radiopaque materials are used and allow for enhanced visualization.

What is claimed is:

1. A buoy system for treating cardiac valve regurgitation, the system comprising:
   a tether element having an atrial end and a ventricular end, the atrial end having a cap and being configured to be inserted into an atrium of a heart;
   a plug having an atrial end and a ventricular end, the plug defining a through-hole therethrough, the through-hole being configured to receive the tether element, and
   a cone disposed on the tether element and configured to be moved by a flow of blood, wherein movement of the cone by the flow of blood causes movement of the buoy system to align with the flow of blood,
      wherein, during a systolic phase of a cardiac cycle, the plug is configured to move along the tether toward the atrial end of the tether element, and
      wherein, during a diastolic phase of the cardiac cycle, the plug is configured to move along the tether element toward the ventricular end of the tether element.

2. The system of claim 1, wherein, during the systolic phase of the cardiac cycle, at least a portion of the plug is configured to align with an annular plane extending through a valve annulus within the heart.

3. The system of claim 2, wherein, when the plug is aligned, the plug is configured to be positioned such that one or more valve leaflets coapt to the plug.

4. The system of claim 3, wherein, during the diastolic phase of the cardiac cycle, the plug is configured to move a distance within the ventricle such that the plug does not cause obstruction across the cardiac valve.

5. The system of claim 4, wherein the plug is configured to move within the ventricle away from the annular plane of the heart, such that the atrial end of the plug is spaced from a plane defined by chordae tendinae in the heart.

6. The system of claim 1, wherein the plug further includes a coaptation zone, wherein the coaptation zone includes an atrial end and a ventricular end, and wherein the coaptation zone of the plug allows for coaptation by anterior and posterior leaflets of the heart valve.

7. The system of claim 6, wherein the plug forms a conical shape, wherein the atrial end of the plug is tapered from the atrial end in a direction toward the ventricular end from a first diameter to a second diameter, wherein the second diameter is greater than the first diameter, wherein the coaptation zone forms a conical shape, and wherein the ventricular end of the plug is flat.

8. A buoy system for treating cardiac valve regurgitation comprising:
   a plug having an atrial end and a ventricular end, the plug defining a through-hole extending from the atrial end to the ventricular end,
   a tether element having an atrial end and a ventricular end, the tether element being receivable into the through-hole of the plug such that the plug is configured to move along the tether element,
      wherein, during a systolic phase of a cardiac cycle, the plug is configured to move along the tether toward the atrial end of the tether element,
      wherein, during a diastolic phase of the cardiac cycle, the plug is configured to move along the tether element toward the ventricular end of the tether element;
         wherein the atrial end of the tether element includes a cap and is configured to be inserted into an atrium of a heart,
      wherein the tether element includes at least one distal anchor at the ventricular end of the tether element, the at least one discal anchor being configured to be disposed in a ventricle of the heart, and
      wherein a cone is disposed on the tether element and configured to be moved by a flow of blood, wherein movement of the cone by the flow of blood causes movement of the buoy system to align with the flow of blood.

9. The system of claim 8, wherein, during the systolic phase of the cardiac cycle, at least a portion of the plug is configured to align with an annular plane extending through a valve annulus within the heart.

10. The system of claim 9, wherein, when the plug is aligned, the plug is configured to be positioned such that one or more valve leaflets coapt to the plug.

11. The system of claim 10, wherein, during the diastolic phase of the cardiac cycle, the plug is configured to move a distance within the ventricle such that the plug does not cause obstruction across the cardiac valve.

12. The system of claim 11, wherein the plug is configured to move within the ventricle away from the annular plane of the heart, such that the atrial end of the plug is spaced from a plane defined by chordae tendinae in the heart.

13. The system of claim 8, wherein the plug further includes a coaptation zone, wherein the coaptation zone includes an atrial end and a ventricular end, and wherein the coaptation zone of the plug allows for coaptation by anterior and posterior leaflets of the heart valve.

14. The system of claim 13, wherein the plug forms a conical shape, wherein the atrial end of the plug is tapered from the atrial end in a direction toward the ventricular end from a first diameter to a second diameter, wherein the second diameter is greater than the first diameter, wherein the coaptation zone forms a conical shape, and wherein the ventricular end of the plug is flat.

15. A device for treating cardiac valve regurgitation, the device operable to be disposed in a heart valve, the heart valve having a plurality of leaflets, each of the plurality of leaflets having a leaflet end, the heart valve being configured to transition between an open configuration and a closed configuration, the device comprising:
   a tether element having an atrial end and a ventricular end, the ventricular end being configured to be disposed between an atrium and a ventricle of the heart;
   wherein, when the valve is in the closed configuration, the valve and the plurality of leaflets form a closed valve plane, and
   when the valve is in the open configuration, the leaflet ends of the plurality of leaflets form an open valve plane;
   the device further comprising a main body disposed along the tether element and configured to be moved along the tether element,
   wherein, when the valve is in the closed configuration, the plurality of leaflets of the heart valve coapt onto the main body, and
   when the valve is in the open configuration, the main body is spaced from the open valve plane so as not to obstruct the valve;
   the device further comprising at least one ventricular anchor disposed at the ventricular end of the tether element,
   wherein at least one anchor stopper is disposed proximal to the at least one ventricular anchor, and
   wherein the at least one ventricular anchor is configured to be attached to the heart, and
   wherein a cone is disposed on the tether element and configured to be moved by a flow of blood, wherein movement of the cone by the flow of blood causes movement of the device to align with the flow of blood.

16. The device of claim 15, wherein the tether element includes a cap disposed at the atrial end, and wherein the cap includes a mechanism for recapture of the device.

17. The device of claim 15, wherein the tether element is solid throughout the length of the element.

18. The device claim 15, wherein the tether element includes a flexible portion and an inflexible portion.

19. The device claim 15, wherein the main body includes an atrial end and a ventricular end, and wherein a first through-hole passes from the atrial end to the ventricular end.

20. The device of claim 15, wherein during a systolic phase of a cardiac cycle, the main body is configured to travel toward a cardiac valve and is configured to be disposed across and within the closed valve plane.

21. The device of claim 1, wherein the plug includes a deformable material configured to be deformed by a leaflet of a heart valve.

22. The device of claim 1, wherein the plug includes an anti-thrombogenic coating along the through-hole.

23. The device of claim 1, further comprising a washer coupled to the plug, the washer being configured to prevent blood from entering the through-hole of the plug during movement of the plug along the tether element,
   wherein the through-hole of the plug has a first diameter, the washer has a second diameter, and the second diameter is smaller than the first diameter.

24. The device of claim 23, wherein the washer is coupled to the ventricular end of the plug.

25. The device of claim 23, wherein the plug includes a radiopaque material.

26. The device of claim 1, further comprising a stopper disposed on the tether element between the plug and the ventricular end or the atrial end of the tether element, the stopper being configured to be contacted by the plug during movement of the plug along the tether element such that the plug is precluded from moving past the stopper.

* * * * *